United States Patent
Saponas et al.

(10) Patent No.: US 11,344,214 B2
(45) Date of Patent: *May 31, 2022

(54) WEARABLE PULSE PRESSURE WAVE SENSING DEVICE

(71) Applicant: Microsoft Technology Licensing, LLC, Redmond, WA (US)

(72) Inventors: T. Scott Saponas, Woodinville, WA (US); Dan Morris, Bellevue, WA (US); Nicolas Villar, Cambridge (GB); Shwetak Patel, Seattle, WA (US); Greg R. Smith, Bellevue, WA (US); Desney Tan, Kirkland, WA (US); Orestis Vardoulis, Lausanne (CH); Sidhant Gupta, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/915,212

(22) Filed: Jun. 29, 2020

(65) Prior Publication Data

US 2020/0329987 A1 Oct. 22, 2020

Related U.S. Application Data

(63) Continuation of application No. 14/500,459, filed on Sep. 29, 2014, now Pat. No. 10,694,960.

(51) Int. Cl.
*A61B 5/024* (2006.01)
*A61B 5/00* (2006.01)
(Continued)

(52) U.S. Cl.
CPC ........ *A61B 5/02438* (2013.01); *A61B 5/0059* (2013.01); *A61B 5/02007* (2013.01);
(Continued)

(58) Field of Classification Search
CPC ..... A61B 8/04; A61B 5/02438; A61B 5/0059; A61B 5/02007; A61B 5/02405;
(Continued)

(56) References Cited

U.S. PATENT DOCUMENTS

2003/0212335 A1* 11/2003 Huang .................. A61B 5/021
600/500

FOREIGN PATENT DOCUMENTS

JP 2014064666 A 4/2014

OTHER PUBLICATIONS

"Office Action Issued in Chinese Patent Application No. 201580052581. 6", dated Jun. 30, 2020, 7 Pages.
(Continued)

*Primary Examiner* — Carolyn A Pehlke
(74) *Attorney, Agent, or Firm* — Alleman Hall Creasman & Tuttle LLP (57) ABSTRACT

Wearable pulse pressure wave sensing devices are presented that generally provide a non-intrusive way to measure a pulse pressure wave travelling through an artery using a wearable device. In one implementation, the device includes an array of pressure sensors disposed on a mounting structure which is attachable to a user on an area proximate to an underlying artery. Each of the pressure sensors is capable of being mechanically coupled to the skin of the user proximate to the underlying artery. In addition, there are one or more arterial location sensors disposed on the mounting structure which identify a location on the user's skin likely overlying the artery. A pulse pressure wave is then measured using the pressure sensor of the array closest to the identified location.

15 Claims, 6 Drawing Sheets

(51) Int. Cl.
*A61B 5/02* (2006.01)
*A61B 8/08* (2006.01)
*A61B 5/107* (2006.01)

(52) U.S. Cl.
CPC .......... *A61B 5/02405* (2013.01); *A61B 5/681* (2013.01); *A61B 5/721* (2013.01); *A61B 5/1079* (2013.01); *A61B 8/085* (2013.01); *A61B 2562/0247* (2013.01); *A61B 2562/046* (2013.01)

(58) Field of Classification Search
CPC ......... A61B 5/681; A61B 5/721; A61B 5/021; A61B 5/022; A61B 5/02108; A61B 5/02116; A61B 5/02255; A61B 5/026; A61B 8/02; A61B 8/06; A61B 6/4233; A61B 2562/024704
See application file for complete search history.

(56) References Cited

OTHER PUBLICATIONS

"Office Action Issued in Korean Patent Application No. 10-2017-7011397", dated Dec. 14, 2021, 7 Pages.
"Notice of Allowance Issued in Korean Patent Application No. 10-2017-7011397", dated Apr. 6, 2022, 7 Pages.

* cited by examiner

WEARABLE PULSE PRESSURE WAVE SENSING DEVICE

CROSS REFERENCE TO RELATED APPLICATIONS

This application is a continuation of U.S. patent application Ser. No. 14/500,459, filed Sep. 29, 2014, the entirety of which is hereby incorporated herein by reference for all purposes.

BACKGROUND

Heart disease is the leading cause of death in the United States, accounting for around six hundred thousand deaths per year (nearly 31% of reported deaths in the United States). High blood pressure (hypertension) is one of the most well-understood risk factors for heart disease. Hypertension is a risk factor for stroke, heart attack, heart failure, arterial aneurysm, and is the leading cause of renal failure. In the United States alone, it is estimated that hypertension incurs billions in direct, yearly healthcare costs, and nearly 1,000 deaths daily. Hypertension is a significant public health issue, and nothing would save more lives than getting blood pressure under control.

Unfortunately, hypertension has no visible warning signs or symptoms, and many people do not even realize they have it. This is particularly unfortunate because hypertension is treatable: lifestyle changes, specifically diet and exercise, are known to be effective in preventing the progression of hypertension. Moreover, numerous medications are available to treat hypertension. Therefore, the key to preventing many heart disease-related deaths may simply be awareness of the risk.

Despite this, blood pressure readings have not gained much attention in the consumer space. Hypertension is still typically identified through infrequent screening (e.g., at an annual exam, health fair, etc.) or when seeking healthcare for an unrelated medical issue.

SUMMARY

The wearable pulse pressure wave sensing device implementations described herein generally provide a non-intrusive way to measuring a pulse pressure wave travelling through an artery using a wearable device. In one implementation, the device includes a mounting structure which is attachable to a user on an area proximate to an underlying artery. On this mounting structure is disposed an array of pressure sensors, each of which is capable of being mechanically coupled to the skin of the user proximate to the underlying artery. In addition, there are one or more arterial location sensors disposed on the mounting structure which identify a location on the user's skin likely overlying the artery. The pulse pressure wave is measured using the pressure sensor of the array closest to the identified location.

It should be noted that the foregoing Summary is provided to introduce a selection of concepts, in a simplified form, that are further described below in the Detailed Description. This Summary is not intended to identify key features or essential features of the claimed subject matter, nor is it intended to be used as an aid in determining the scope of the claimed subject matter. Its sole purpose is to present some concepts of the claimed subject matter in a simplified form as a prelude to the more detailed description that is presented below.

DESCRIPTION OF THE DRAWINGS

The specific features, aspects, and advantages of the disclosure will become better understood with regard to the following description, appended claims, and accompanying drawings where:

DETAILED DESCRIPTION

In the following description of wearable pulse pressure wave sensing device implementations reference is made to the accompanying drawings which form a part hereof, and in which are shown, by way of illustration, specific versions in which the wearable pulse pressure wave sensing device implementations can be practiced. It is understood that other implementations can be utilized and structural changes can be made without departing from the scope thereof.

It is also noted that for the sake of clarity specific terminology will be resorted to in describing the wearable pulse pressure wave sensing device implementations described herein and it is not intended for these implementations to be limited to the specific terms so chosen. Furthermore, it is to be understood that each specific term includes all its technical equivalents that operate in a broadly similar manner to achieve a similar purpose. Reference herein to "one implementation", or "another implementation", or an "exemplary implementation", or an "alternate implementation" means that a particular feature, a particular structure, or particular characteristics described in connection with the implementation can be included in at least one implementation of pulse pressure wave sensing. The appearances of the phrases "in one implementation", "in another implementation", "in an exemplary implementation", and "in an alternate implementation" in various places in the specification are not necessarily all referring to the same implementation, nor are separate or alternative implementations mutually exclusive of other implementations. Yet furthermore, the order of process flow representing one or more implementations of wearable pulse pressure wave sensing does not inherently indicate any particular order or imply any limitations thereof.

As utilized herein, the terms "component," "system," "client" and the like are intended to refer to a computer-related entity, either hardware, software (e.g., in execution), firmware, or a combination thereof. For example, a component can be a process running on a processor, an object, an executable, a program, a function, a library, a subroutine, a computer, or a combination of software and hardware. By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, to the extent that the terms "includes," "including," "has," "contains," variants thereof, and other similar words are used in either this detailed description or the claims, these terms are intended to be inclusive in a manner similar to the term "comprising" as an open transition word without precluding any additional or other elements.

1.0 Pulse Pressure Wave Sensing

When the human heart expels blood, a pressure wave is created. This pressure wave travels along the arteries in the body affected by the overall blood pressure, the lining of the arteries, and the stiffness/compliance of the arteries. A pressure sensor at a given point in an artery can transduce this pressure as it changes with time and record the resulting pulse pressure wave. The pulse pressure wave is formed from the combination of an incident wave generated by the contraction of the left ventricle of a person's heart and waves reflected back from the periphery of the arterial system. Pressure sensors generally come in two forms: invasive and non-invasive. The invasive form is a catheter inserted in the artery with a pressure sensor on the tip. This type of pressure sensing is the most accurate way to record pulse pressure waves. The non-invasive approach involves placing a pressure sensor on the surface of the skin over an artery and applying force such that the changing intra-arterial pulse pressure is transmitted through the arterial wall to the sensor. Arteries that are commonly sensed non-invasively are the radial, carotid, and femoral arteries (although any other artery located near the surface of the skin can be sensed as well). A pressure sensor used to transduce pulse pressure waves is often called a tonometer. The morphology of a pulse pressure wave sensed by a tonometer can be analyzed to ascertain important information about the state and health of the cardiovascular system, as will be described in more detail in the sections to follow.

1.1 Wearable Pulse Pressure Wave Sensing Device

The wearable pulse pressure wave sensing device implementations described herein are generally applicable to non-invasive tonometric measurement of the aforementioned pulse pressure waves. As will be appreciated from the more detailed description that follows, the wearable pulse pressure wave sensing device implementations described herein are advantageous for various reasons. For example, the wearable pulse pressure wave sensing device implementations described herein facilitate a cost effective and easy way to assess cardiovascular health. The described implementations can also assist in preventing many heart-disease-related deaths by making users who have hypertension aware of it. Once a given user is made aware of their having hypertension, the wearable pulse pressure wave sensing device implementations described herein can facilitate routine monitoring of the user's cardiovascular vital signs, and encourage the user to treat their hypertension by consulting with a doctor and making appropriate lifestyle changes. The described implementations also measure a pulse pressure wave at a location on the body in a non-invasive and non-intrusive (e.g., a passive) manner, and thus allow users to routinely measure/monitor their cardiovascular vital signs without pain and discomfort.

As will also be appreciated from the more detailed description that follows, the wearable pulse pressure wave sensing device implementations described herein can be employed in a variety of applications, and can also be realized in various types of computing devices. The wearable pulse pressure wave sensing device implementations are also easy to operate, and are not restricted to being used by a trained medical technician or doctor in a controlled medical setting such as a laboratory or doctor's office.

Further, as the described implementations are wearable on the body of a user, ambulatory automatic tonometry is possible and thus facilitates the convenient and automatic measurement of cardiovascular vital signs at one or more opportunistic times during the normal course of a day while a user is either stationary or in motion, including while a user is involved in or performing a wide variety of physical activities. As will be appreciated from the more detailed description that follows, the wearable pulse pressure wave sensing device implementations described herein do not require a user to ensure that a pressure sensor directly overlies an artery. Rather, the implementations described herein automatically choose a pressure sensor and senses a tonometry signal without any precise manipulation of the device.

Figure 1:
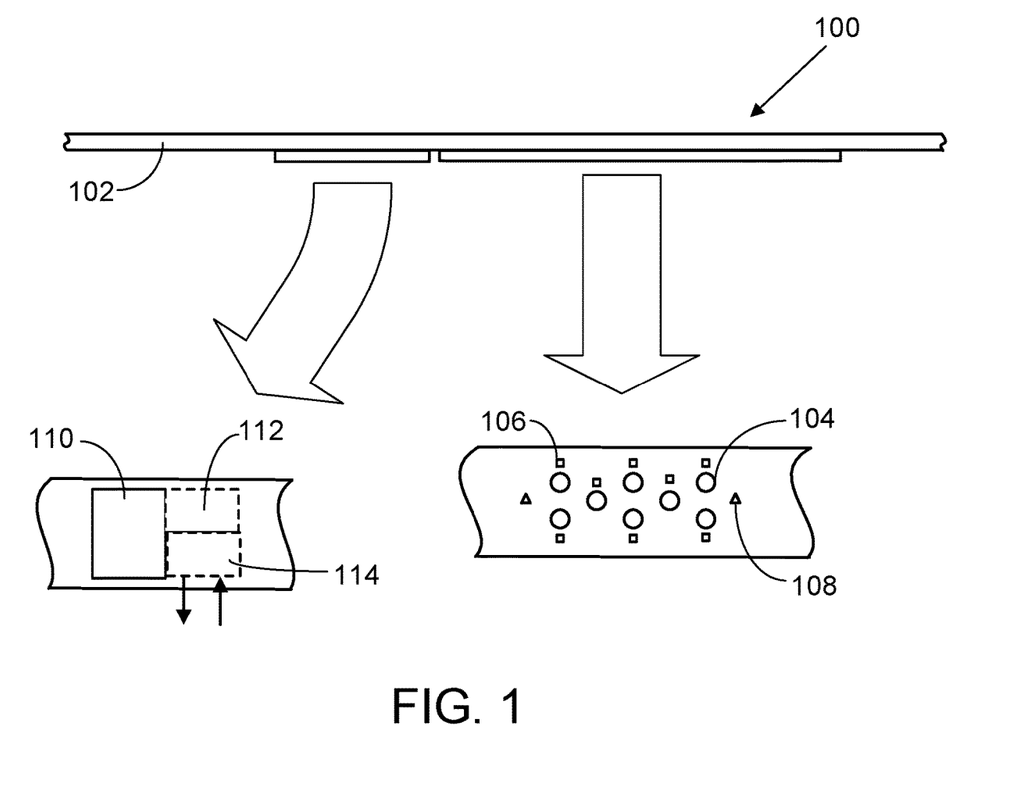
FIG. 1 is a simplified diagram of one exemplary implementation of a wearable pulse pressure wave sensing device.

FIG. 1 illustrates one exemplary implementation of the wearable pulse pressure wave sensing device. The device 100 includes a mounting structure 102 which is attachable to a user on an area proximate to an underlying artery. In addition, the device 100 includes an array of pressure sensors disposed on the mounting structure 102. Each pressure sensor 104 of the array is capable of being mechanically coupled to the skin of the user proximate to the underlying artery. The wearable pulse pressure wave sensing device 100 further includes one or more arterial location sensors 106 (a plurality of which are shown in FIG. 1) disposed on the mounting structure 102 that identify a location on the user's skin likely overlying the artery. A pulse pressure wave travelling through the artery is then measured using the pressure sensor 104 of the array identified as being closest to the identified location.

In one version, the pressure sensors are of the mechanical type, such as, but without limitation, piezoresistive pressure sensors that sense the motion of an underlying artery through the skin when the pulse arrives. The shape of the surface of each pressure sensor that faces the user can be any desired (square, rectangular, triangular, and so on). The pressure sensors can all have the same facing surface, all different facing surfaces, or any combination of facing surfaces.

In one version, the pressure sensors are coated with a skin-sensor interface material that contacts the skin of the user and propagates pressure waves representing the movement of the skin owing to a pulse pressure wave travelling through an artery underlying the sensors. In one version, each pressure sensor is coated individually such that its coating does not extend over any other of the pressure sensors. In another version, two or more of the pressure sensors have a common coating. In one version, the coating is a single layer of cured silicone gel. The profile shape of the coating can be anything practical that ensures adequate contact with the user's skin but does not cause undue discomfort to the user. For example, in one version the coating takes the shape of a spherical cap (or similar curved shape) protruding from the mounting structure. The stiffness of the coating can range between hard and soft. In operation, the coated pressure sensors are pressed down onto the skin of the user to ensure efficient transmission of the motion of the underlying artery to the sensors. A hard coating ensures better transmission of the movements caused by a pulse pressure wave passing through the artery, but even though only a slight pressure is applied to the skin, it would not be as comfortable to the user as a softer coating. Although a soft coating would be more comfortable than a hard coating, it would not transmit the motion as well. Thus, in one version, the coating stiffness is made so as to balance efficient motion transmission with comfort. Alternately, in one version the coated pressure sensors have a multi-layer construction that attempts to maximize the transmission of the movements caused by a pulse pressure wave passing through the artery, while at the same time attempting to maximize the user's comfort. In this version, there is a skin interfacing layer made of a non-sensitizing, hypo-allergenic and non-irritating material (e.g., a soft, cured silicone gel). Between the skin interfacing layer and the pressure sensor is a layer made of a material that optimally transmits the arterial pressure wave movement (e.g., a hard, cured silicone gel).

In one version, the coated pressure sensors protrude from the aforementioned mounting structure with a fixed length. This fixed length can be any desired for each of the coated pressure sensors. In one version, all of the coated pressure sensors have the same length, and in other versions one or more of the coated pressure sensors have a different length in comparison with the other sensors.

Alternately, the coated pressure sensors can be extendable and retractable so as to protrude from the mounting structure with adjustable lengths. In one version, an extendable coated pressure sensor is configured in any appropriate manner to be spring loaded (such as via a pogo pin arrangement). A spring-loaded coated pressure sensor extends out to meet the surface of the skin, and to impart a slight pressure thereon. This same extendable coated pressure measurement sensor scheme can be realized using other methods, such as with electro-mechanical actuators, or micro-fluidic pumps that expand and contract an air or fluid-filled bladder (which in turn extends and retract a coated pressure sensor). In the latter two versions, the distance that the coated pressure sensors are extended and the amount of pressure they exert on the skin can be controlled and set to a level that ensures efficient transmission of arterial motion, while not causing discomfort to the user.

The array of pressure sensors can form any desired pattern. For example, in one version, the sensors form a line that can be oriented in any direction relative the user's body. In another version, three pressure sensors are employed to form a triangular pattern. This version can provide a larger effective "field of view" of the underlying artery than the linear version. For the purposes of this description, the phrase "field of view" refers to the area covered by the sensors. In yet another version, a grid of four or more pressure sensors is employed (such as shown in FIG. 1). The grid can exhibit rectangular, triangular, or random spacing of the sensors. The sensors can also be smaller in order to fit more in the available space.

In one version, the aforementioned mounting structure onto which the coated pressure sensors are disposed is capable of being held in place on the user in such a way that the coated sensors are in contact with the skin of the user in the vicinity of an underlying artery and apply a downward pressure. For example, in one version, the coated pressure sensors are mounted on a side of a band that is adhered to, or wrapped around and tightened against (via any appropriate fastening scheme that the tightness is dynamically adjustable), a portion of a user's body overlying an artery. In the case where the band is wrapped around a portion of the user's body, it can be configured to wrap around a person's wrist (like a watch), or forearm, or upper arm (like an armband commonly used to hold mobile phones or music players during exercise), or torso, or upper leg, or lower leg, or ankle, among other places. In general, any place on a person's body that a strap can be wrapped around and tightened, and which movement in an underlying artery can be sensed, would be a viable location. In the case where the band is adhered to the body, not only are the foregoing locations feasible but others as well.

In one version, the location on the band where the pressure sensors are mounted on the mounting structure is flexible so as to readily conform to the contours of the portion of the user's body the band covers. In another version, the location on the band where the pressure sensors are mounted on the mounting structure is rigid. For example, the band can include a rigid platform for mounting the pressure sensors which has flexible portions extending in both directions for attaching it to the body of the user. In the case where the band is attached around the user's wrist, it can resemble a watch with the watch body forming the aforementioned rigid portion. The former flexible version is advantageous in that the coated pressure sensors are better able to contact the surface of the user's skin and remain in contact when slight pressure is applied thereto (such as by tightening the strap which is wrapped around a portion of the user's body). This ensures an efficient transfer of arterial motion to the pressure sensors and can be more comfortable to the user than a rigid version. However, the realization of the aforementioned rigid version is less complicated owing to the aforementioned rigid mounting platform, albeit with possibly varying contact and contact pressure between the coated pressure sensors.

1.1.1 Identifying the Pressure Sensor Closest to the Identified Location

One or more arterial location sensors are employed to identify a location on the user's skin likely overlying the artery being measured. This information is then used to identify the pressure sensor of the array that is closest to the identified location. As indicated previously, the user is not required to precisely place the wearable pulse pressure wave sensing device so that one of its pressure sensors directly overlies an artery. Thus, it is advantageous to automatically identify which of the pressure sensors is closest to the likely location of an underlying artery because a pressure sensor located nearest an artery will typically sense the motion caused by a pulse pressure wave passing through the artery at that location better than a pressure sensor that is placed on the skin at a location offset from the underlying artery.

In one version, the arterial location sensor(s) are employed to identify where on the portion of the user's body covered by the wearable pulse pressure wave sensing device that maximum skin displacement occurs as a pulse pressure wave passes through the underlying artery. The location of maximum skin displacement is deemed to be a probable location of an underlying artery. In one version, the arterial location sensors take the form of reflected optical sensors (e.g., the type employing a light emitting diode (LED) and photodiode). In another version, the arterial location sensors take the form of ultrasonic sensors.

Figure 2:
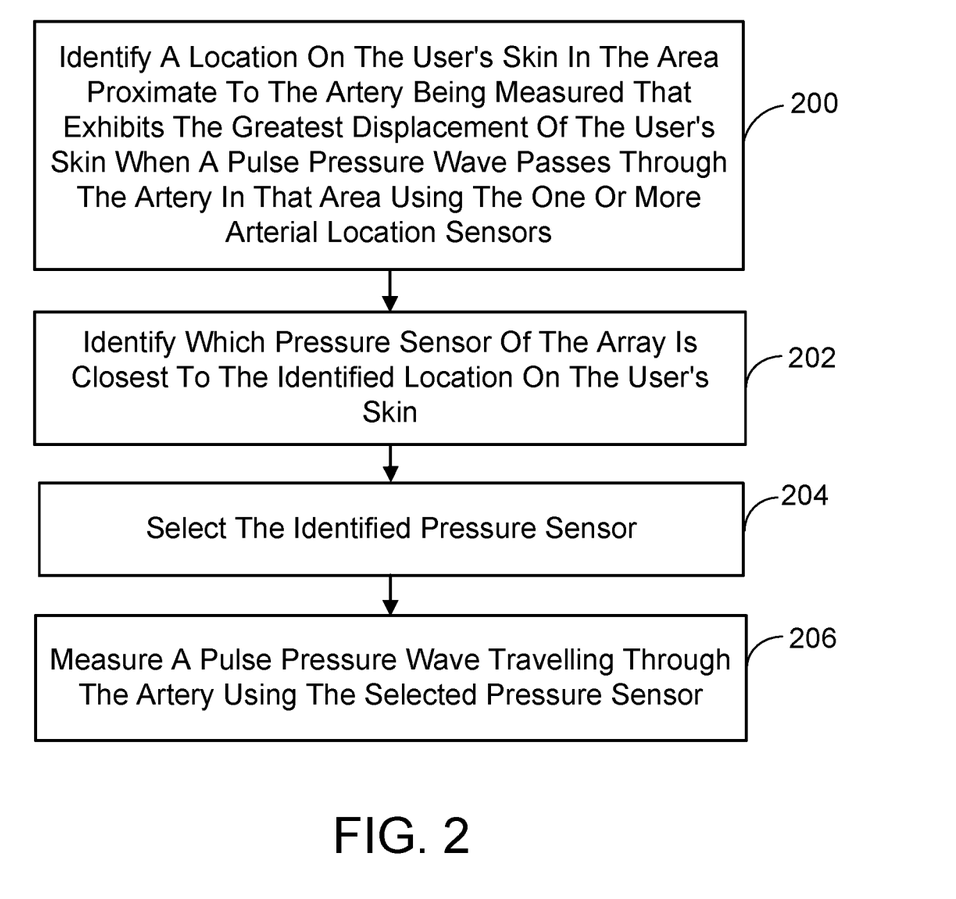
FIG. 2 is a flow diagram illustrating an exemplary implementation, in simplified form, of a process for measuring a pulse pressure wave travelling through an artery using the wearable pulse pressure wave sensing device implementations described herein.

In operation, a computer-implemented process can be used to measure a pulse pressure wave travelling through an artery. Referring to FIG. 2, in one version, a computing device (such as an appropriate one described in the forthcoming exemplary operating environments section) employs the one or more arterial location sensors to identify a location on the user's skin in the area proximate to the artery being measured that exhibits the greatest displacement of the user's skin when a pulse pressure wave passes through the artery in that area (process action 200). For example, in the case where the arterial location sensors are reflected optical sensors or ultrasonic sensors, conventional displacement measuring methods can be employed to accomplish the foregoing task. It is then determined which pressure sensor of the array of pressure sensors is closest to the identified location on the user's skin (process action 202). That pressure sensor is selected (process action 204), and a pulse pressure wave travelling through the artery is measured using the selected pressure sensor (process action 206).

Figure 3:
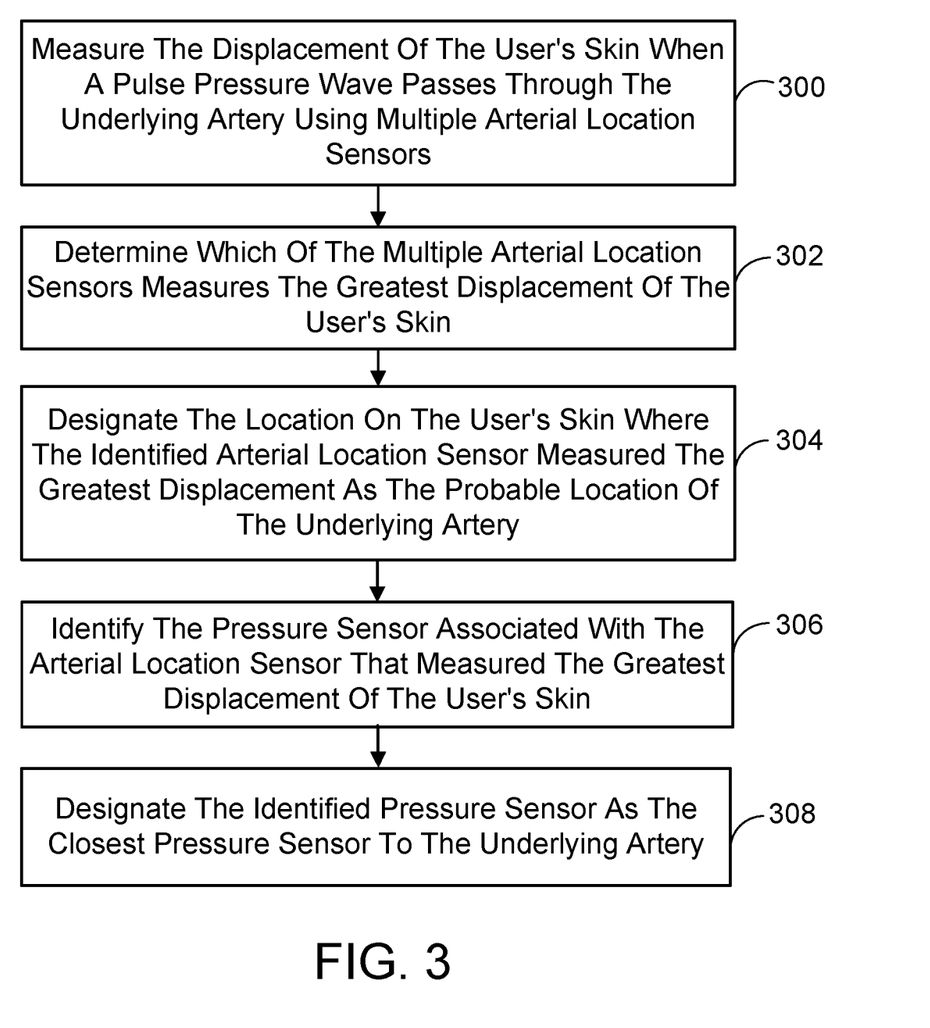
FIG. 3 is a flow diagram illustrating an exemplary implementation, in simplified form, of a process for employing a plurality of arterial location sensors, each one of which is located adjacent to a pressure sensor, to identify a location on the user's skin likely overlying an artery being measured and using this information to identify the pressure sensor of the array that is closest to the identified location.

In one version, a plurality of arterial location sensors are used to identify the aforementioned probable location of the underlying artery. In this version, each pressure sensor has an adjacently-located arterial location sensor (such as shown in FIG. 1). If a particular arterial location sensor measures a skin displacement that is greater than the other arterial location sensors, then its adjacently-located pressure sensor is designated the closest pressure sensor to the underlying artery. More particularly, referring to FIG. 3, in one implementation the following process is employed to find the closest pressure sensor. First, multiple arterial location sensors are employed to measure the displacement of the user's skin when a pulse pressure wave passes through the underlying artery (process action 300). Each arterial location sensor is associated with and located adjacent to a different pressure sensor of the array of pressure sensors. It is then determined which of the multiple arterial location sensors measures the greatest displacement of the user's skin (process action 302). The location on the user's skin where the identified arterial location sensor measured the greatest displacement is then designated as the probable location of the underlying artery (process action 304). The pressure sensor associated with the arterial location sensor that measured the greatest displacement of the user's skin is then identified (process action 306), and is designated as the closest pressure sensor to the underlying artery (process action 308).

Figure 4:
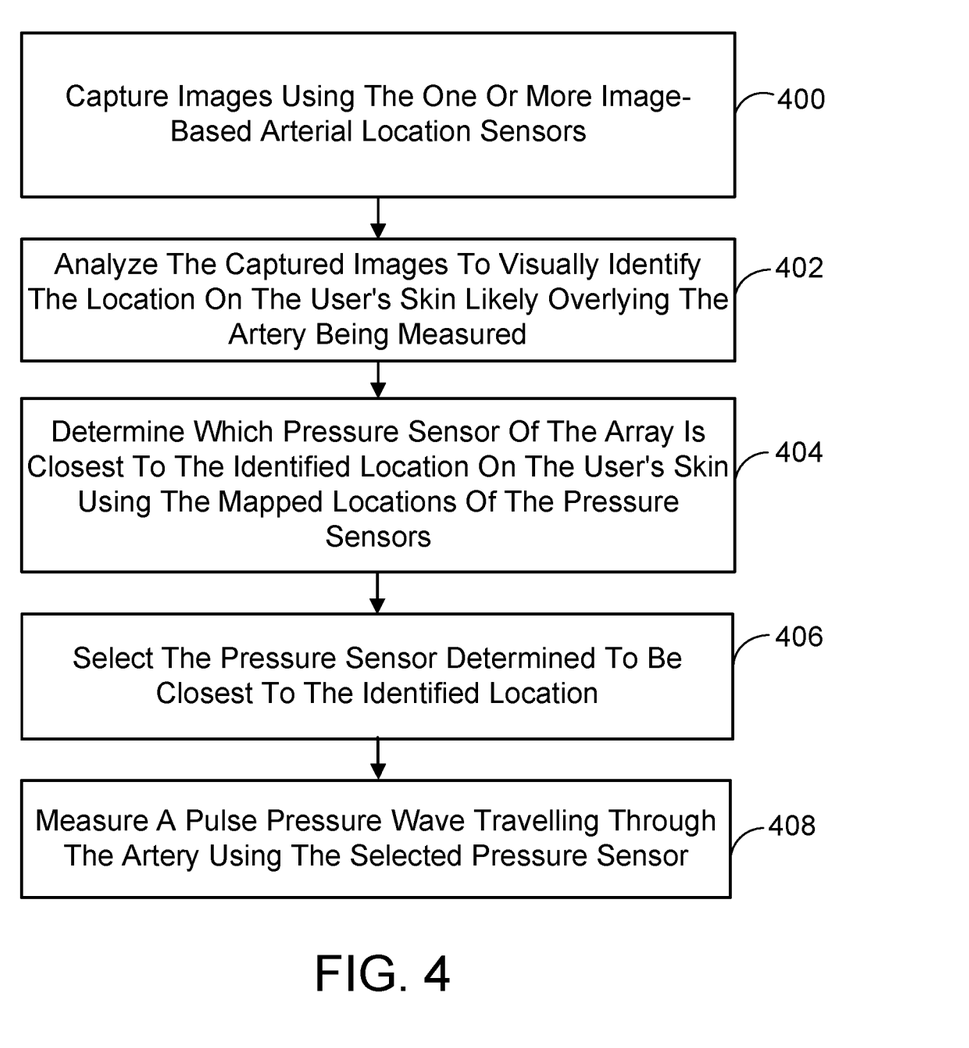
FIG. 4 is a flow diagram illustrating an exemplary implementation, in simplified form, of a process for employing a plurality of image-based arterial location sensors to identify a location on the user's skin likely overlying an artery being measured and using this information to identify the pressure sensor of the array that is closest to the identified location.

In one version, one or more image-based arterial location sensors (e.g., visible or infrared light charge-coupled devices) are used to identify the aforementioned probable location of the underlying artery. In this version, the image-based sensors are mounted around or near the pressure sensor array, and calibrated using conventional methods so that pixels in the images captured are mapped to physical locations relative to each pressure sensor of the array. Given this configuration, referring to FIG. 4, in one implementation the following process is employed to select a pressure sensor and use it to measure a pulse pressure wave travelling through an artery. Images are captured using the one or more image-based arterial location sensors (process action 400). Conventional image analysis is then applied to the captured images to visually identify the location on the user's skin likely overlying the artery being measured (process action 402). It is next determined which pressure sensor of the array of pressure sensors is closest to the identified location on the user's skin using the aforementioned mapped locations of the pressure sensors (process action 404). That pressure sensor is selected (process action 406), and a pulse pressure wave travelling through the artery is measured using the selected pressure sensor (process action 408).

It is noted that in any of the foregoing arterial location sensor versions, once one of the pressure sensors is selected, the other pressure sensors can optionally be turned off. Further, if the other pressure sensors are turned off, they can be periodically reactivated and the appropriate foregoing process repeated to select the pressure sensor that will be used to measure future pulse pressure waves travelling through an artery.

1.1.2 Removing Non-Arterial Motion Contribution

It is noted that the pressure sensors not only measure arterial movements, but also noise owing to other movements of the user. As the wearable pulse pressure wave sensing device is meant to be worn by the user for extended periods of time, the user may be in motion when a pulse pressure wave is measured. In the case of piezoresistive pressure sensors, this ambulatory motion will be sensed and is indistinguishable from arterial motion. To compensate for this noise motion, the signal output by a pressure sensor is filtered to remove as much non-arterial motion contribution as possible.

In one version, the non-arterial motion contribution in the signal is filtered out using the pressure sensor signals themselves. In simplified terms, this entails using conventional methods to identify the part of the output signal in each pressure sensor that is substantially consistent across the sensors. This consistent contribution approximates the non-arterial motion contribution since it should be similar for each sensor, whereas the arterial motion contribution will vary amongst the pressure sensors depending on their relative locations from the underlying artery. The non-arterial motion contribution to the signal of the pressure sensor previously identified as being closest to the likely location of the underlying artery is then subtracted out using conventional signal processing methods, leaving an approximation of the arterial motion contribution. This arterial motion contribution portion of the output signal will exhibit a well-known pulse waveform whose morphology can be analyzed to derive a plurality of cardiovascular metrics as will be described in more detail later in this description.

In alternate versions, the non-arterial motion contribution in the pressure sensor signals is filtered out using one or more non-arterial motion sensors. More particularly, referring once again to FIG. 1, in one version, the aforementioned wearable pulse pressure wave sensing device 100 also includes one or more non-arterial motion sensors 108 (two of which are shown in FIG. 1) disposed on the mounting structure 102. The non-arterial motion sensor(s) 108 measure the motion of the user's body in the area proximate to the underlying artery that is not caused by motion of the artery. The non-arterial movement signal derived from the non-arterial motion sensor(s) 108 is then removed from the signal of the pressure sensor previously identified as being closest to the likely location of the underlying artery using conventional signal processing methods. This leaves an approximation of the arterial motion contribution. As indicated previously, this arterial motion contribution portion of the output signal will exhibit a well-known pulse waveform whose morphology can be analyzed to derive a plurality of cardiovascular metrics.

In one implementation, an accelerometer or gyroscope, or both, are employed as the non-arterial motion sensors. The accelerometer directly measures the non-arterial movement that introduces noise into the pressure senor output signals. A gyroscope measures angular movement, but the output can be readily analyzed using conventional methods to derive linear values similar to those measured by an accelerometer. In cases where both an accelerometer and gyroscope are employed the accelerometer output and the converted gyroscope output can be combined in any appropriate conventional manner to produce a consensus signal representing non-arterial movement.

1.1.3 Cardiovascular Metrics

As indicated previously, the pulse waveforms extracted from the output signal of the pressure sensor selected as closest to the likely location of an underlying artery can be analyzed using conventional methods to measure various cardiovascular metrics. For example, but without limitation, the pulse waveforms can be used to determine the heart rate of a person wearing the pulse pressure wave sensing device, as well as variations in the person's hear rate over time. In addition, an extracted pulse waveform can be used to compute a person's augmentation index. The augmentation index measures how hard the heart is working against the pressure waves reflected back by the periphery of the circulatory system.

The time of arrival of a pulse pressure wave is also useful information and can be determined from the pulse waveform. This arrival time can be used in conjunction with other data to calculate pulse transit time (PTT) and pulse wave velocity (PWV). Generally speaking, PTT refers to the amount of time it takes for a pulse pressure wave that is generated by blood being expelled from a user's heart to travel through the user's arteries from one arterial site on the user's body to another arterial site on the user's body. For example, in the wearable pulse pressure wave sensing device implementations described herein where the device attaches to a user's wrist, the PTT refers to the amount of time it takes for a pulse pressure wave to travel from the user's heart, through their arteries, to an artery on the wrist (e.g., radial artery). As is appreciated in the arts of medicine and cardiovascular health, there is a known correlation between pulse-transit time and other cardiovascular metrics such as blood pressure, arterial compliance, and the hardening of artery walls. Although other body metrics (such as the user's height, weight and age, and the arterial distance between the just-described two arterial sites on the user's body, among other types of body metrics) influence the user's blood pressure, the PTT measurement can be used to determine the user's blood pressure based on the just-described known correlation between PTT and blood pressure.

As for PWV, this term is used to refer to the speed at which a pulse pressure wave travels through a user's arteries from one arterial site on the user's body to another arterial site on the user's body. In the previously-described exemplary version where the pulse pressure wave sensing device is worn on a user's wrist, PWV refers to the average speed at which the pulse pressure wave travels from the user's heart, through their arteries, to the wrist. As is appreciated in the arts of medicine and cardiovascular health, there is a known correlation between pulse-wave velocity and cardiovascular diseases such as hypertension. More particularly, as a person ages their arteries generally get stiffer. This increasing arterial stiffness makes the person's heart work harder and also makes the pulse pressure wave travel faster through their arteries, thus increasing their risk of cardiovascular diseases such as hypertension.

Computation of the foregoing cardiovascular metrics, along with the previously-described processing of the signals output from the pressure sensors, arterial location sensor(s) and non-arterial motion sensor(s) is accomplished in one implementation using one or more computing devices (such as one of those described in the forthcoming exemplary operating environments section), and a computer program executing thereon. Referring again to FIG. 1, in one implementation, the wearable pulse pressure wave sensing device 100 also includes a computing device 110 disposed on the mounting structure 102 that is employed for the foregoing processing and computations. In addition, the wearable pulse pressure wave sensing device 100 can optionally include an appropriate conventional storage component 112 for storing any data needed to accomplish the aforementioned processing and computations, as well storing the results of the processing and computations. Still further, the wearable pulse pressure wave sensing device 100 can optionally include an appropriate conventional communications component 114 for communicating with the remote computing devices. For example, the communications component can be employed to receive data needed to perform the aforementioned processing and computations, or to transmit computed cardiovascular metrics. Any communication scheme can be employed. For example, communication can be via a computer network such as the Internet or a proprietary intranet. It is noted that the dashed-line boxes used in FIG. 1 indicate optional components.

Figure 5:
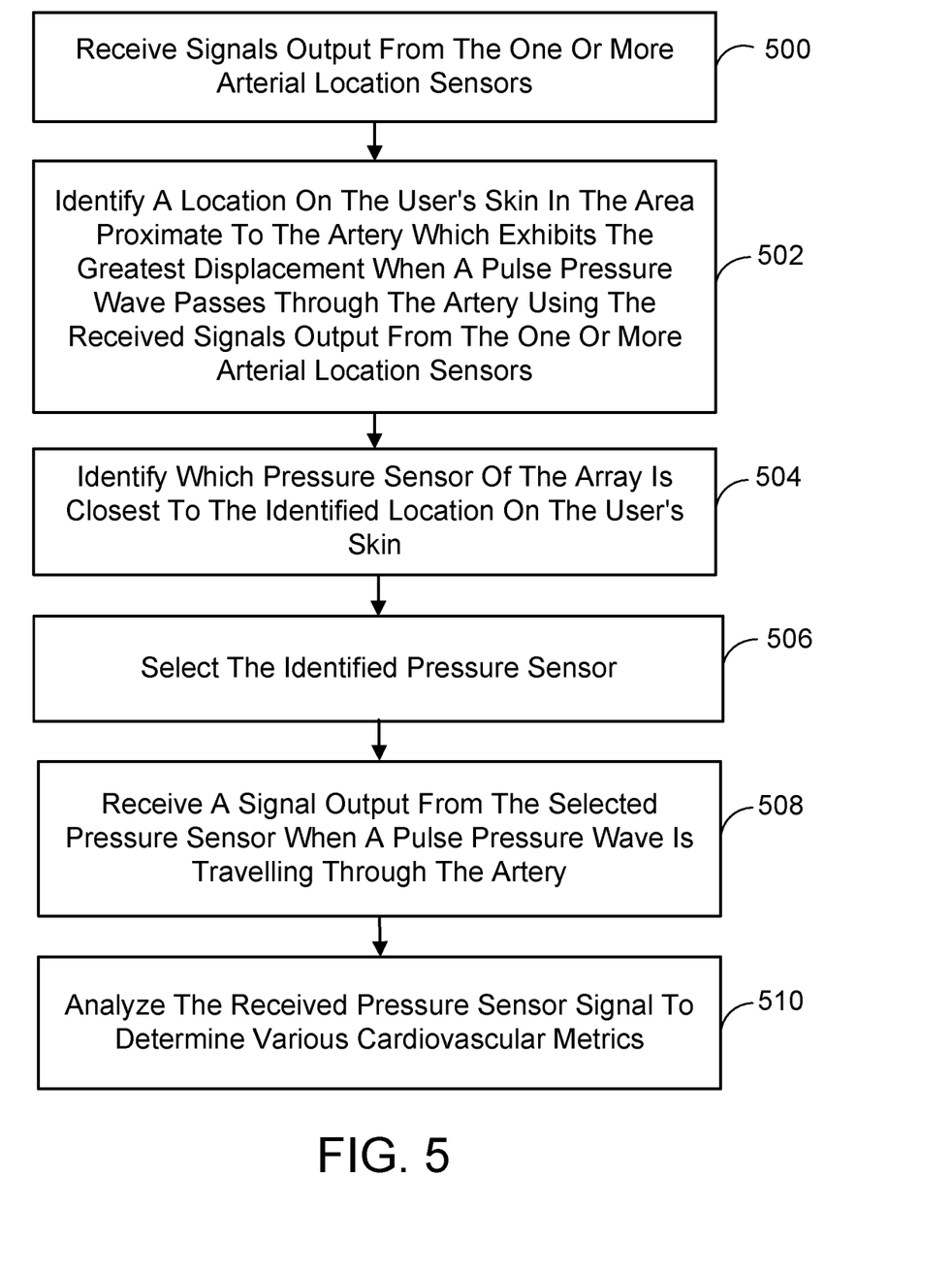
FIG. 5 is a flow diagram illustrating an exemplary implementation, in simplified form, of a process for measuring a pulse pressure wave and using the morphology of the wave to compute various cardiovascular metrics.

In view of the foregoing and referring to FIG. 5, in one version, the computing device is directed by the program modules of the computer program to first receive signals output from the one or more arterial location sensors (process action 500). A location on the user's skin in the area proximate to the artery which exhibits the greatest displacement when a pulse pressure wave passes through the artery is then identified using the received signals output from the one or more arterial location sensors (process action 502). It is next determined which pressure sensor of the array of pressure sensors is closest to the identified location on the user's skin (process action 504), and that pressure sensor is selected (process action 506). A signal output from the selected pressure sensor when a pulse pressure wave is travelling through the artery is received (process action 508), and it is analyzed to determine various cardiovascular metrics (process action 510). These metrics can be stored or transmitted, or both.

1.1.4 Wrist-Band Implementations

As indicated previously, the wearable pulse pressure wave sensing device implementations described herein include versions that are worn on the wrist. These wrist-band versions provide an opportunity to include additional advantageous features and configurations. For example, in one version, the wrist-band takes the form of a wrist watch, and in another the wrist-band takes the form of a so-called "smart watch" with all its attendant computing, display and communication capabilities. It is noted that given the user interface capabilities of a smart watch, the wearable sensing implementations described herein employing this form can be configured via conventional means to display information to the wearer. For example, instructions for operating the wrist-band implementations can be displayed to the user, as well as the computed cardiovascular metrics.

It is further noted that given the proximity of the underside (i.e., palm side) of the wrist to arteries (such as the radial artery), placement of the pressure sensors, arterial location sensor(s) and non-arterial motion sensor(s) on the part of a watchband that touches this portion of the wrist is advantageous.

2.0 Exemplary Operating Environments

Figure 6:
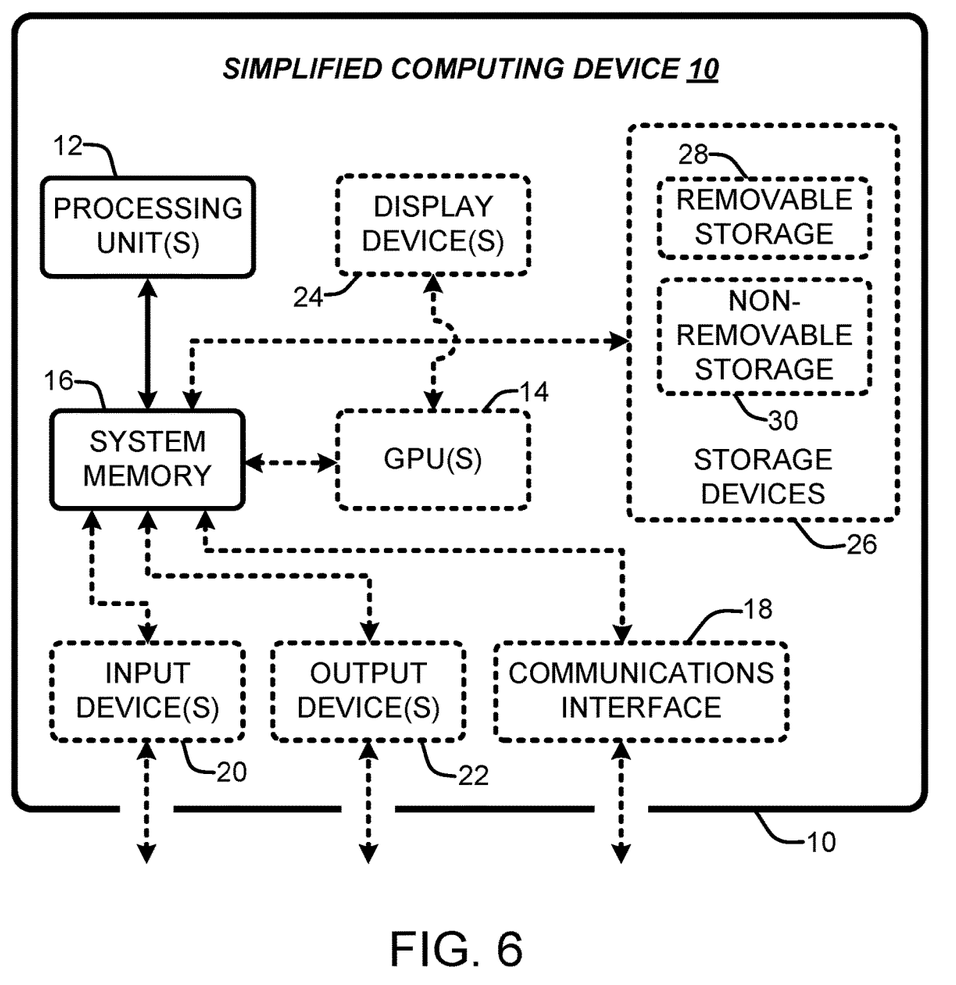
FIG. 6 is a diagram depicting a general purpose computing device constituting an exemplary system for use with the wearable pulse pressure wave sensing device implementations described herein.

The wearable pulse pressure wave sensing device implementations described herein are operational using numerous types of general purpose or special purpose computing system environments or configurations. FIG. 6 illustrates a simplified example of a general-purpose computer system with which various aspects and elements of wearable pulse pressure wave sensing device, as described herein, may be implemented. It is noted that any boxes that are represented by broken or dashed lines in the simplified computing device 10 shown in FIG. 6 represent alternate implementations of the simplified computing device. As described below, any or all of these alternate implementations may be used in combination with other alternate implementations that are described throughout this document. The simplified computing device 10 is typically found in devices having at least some minimum computational capability such as personal computers (PCs), server computers, handheld computing devices, laptop or mobile computers, communications devices such as cell phones and personal digital assistants (PDAs), multiprocessor systems, microprocessor-based systems, set top boxes, programmable consumer electronics, network PCs, minicomputers, mainframe computers, and audio or video media players.

To realize the wearable pulse pressure wave sensing device implementations described herein, the device should have a sufficient computational capability and system memory to enable basic computational operations. In particular, the computational capability of the simplified computing device 10 shown in FIG. 6 is generally illustrated by one or more processing unit(s) 12, and may also include one or more graphics processing units (GPUs) 14, either or both in communication with system memory 16. Note that that the processing unit(s) 12 of the simplified computing device 10 may be specialized microprocessors (such as a digital signal processor (DSP), a very long instruction word (VLIW) processor, a field-programmable gate array (FPGA), or other micro-controller) or can be conventional central processing units (CPUs) having one or more processing cores.

In addition, the simplified computing device 10 may also include other components, such as, for example, a communications interface 18. The simplified computing device 10 may also include one or more conventional computer input devices 20 (e.g., touchscreens, touch-sensitive surfaces, pointing devices, keyboards, audio input devices, voice or speech-based input and control devices, video input devices, haptic input devices, devices for receiving wired or wireless data transmissions, and the like) or any combination of such devices.

Similarly, various interactions with the simplified computing device 10 and with any other component or feature of wearable sensing, including input, output, control, feedback, and response to one or more users or other devices or systems associated with wearable sensing, are enabled by a variety of Natural User Interface (NUI) scenarios. The NUI techniques and scenarios enabled by wearable sensing include, but are not limited to, interface technologies that allow one or more users user to interact with wearable sensing in a "natural" manner, free from artificial constraints imposed by input devices such as mice, keyboards, remote controls, and the like.

Such NUI implementations are enabled by the use of various techniques including, but not limited to, using NUI information derived from user speech or vocalizations captured via microphones or other sensors. Such NUI implementations are also enabled by the use of various techniques including, but not limited to, information derived from a user's facial expressions and from the positions, motions, or orientations of a user's hands, fingers, wrists, arms, legs, body, head, eyes, and the like, where such information may be captured using various types of 2D or depth imaging devices such as stereoscopic or time-of-flight camera systems, infrared camera systems, RGB (red, green and blue) camera systems, and the like, or any combination of such devices. Further examples of such NUI implementations include, but are not limited to, NUI information derived from touch and stylus recognition, gesture recognition (both onscreen and adjacent to the screen or display surface), air or contact-based gestures, user touch (on various surfaces, objects or other users), hover-based inputs or actions, and the like. Such NUI implementations may also include, but are not limited, the use of various predictive machine intelligence processes that evaluate current or past user behaviors, inputs, actions, etc., either alone or in combination with other NUI information, to predict information such as user intentions, desires, and/or goals. Regardless of the type or source of the NUI-based information, such information may then be used to initiate, terminate, or otherwise control or interact with one or more inputs, outputs, actions, or functional features of wearable pulse pressure wave sensing device implementations described herein.

However, it should be understood that the aforementioned exemplary NUI scenarios may be further augmented by combining the use of artificial constraints or additional signals with any combination of NUI inputs. Such artificial constraints or additional signals may be imposed or generated by input devices such as mice, keyboards, and remote controls, or by a variety of remote or user worn devices such as accelerometers, electromyography (EMG) sensors for receiving myoelectric signals representative of electrical signals generated by user's muscles, heart-rate monitors, galvanic skin conduction sensors for measuring user perspiration, wearable or remote biosensors for measuring or otherwise sensing user brain activity or electric fields, wearable or remote biosensors for measuring user body temperature changes or differentials, and the like. Any such information derived from these types of artificial constraints or additional signals may be combined with any one or more NUI inputs to initiate, terminate, or otherwise control or interact with one or more inputs, outputs, actions, or functional features of wearable pulse pressure wave sensing device implementations described herein.

The simplified computing device 10 may also include other optional components such as one or more conventional computer output devices 22 (e.g., display device(s) 24, audio output devices, video output devices, devices for transmitting wired or wireless data transmissions, and the like). Note that typical communications interfaces 18, input devices 20, output devices 22, and storage devices 26 for general-purpose computers are well known to those skilled in the art, and will not be described in detail herein.

The simplified computing device 10 shown in FIG. 6 may also include a variety of computer-readable media. Computer-readable media can be any available media that can be accessed by the computer 10 via storage devices 26, and can include both volatile and nonvolatile media that is either removable 28 and/or non-removable 30, for storage of information such as computer-readable or computer-executable instructions, data structures, program modules, or other data. Computer-readable media includes computer storage media and communication media. Computer storage media refers to tangible computer-readable or machine-readable media or storage devices such as digital versatile disks (DVDs), blu-ray discs (BD), compact discs (CDs), floppy disks, tape drives, hard drives, optical drives, solid state memory devices, random access memory (RAM), read-only memory (ROM), electrically erasable programmable read-only memory (EEPROM), CD-ROM or other optical disk storage, smart cards, flash memory (e.g., card, stick, and key drive), magnetic cassettes, magnetic tapes, magnetic disk storage, magnetic strips, or other magnetic storage devices. Further, a propagated signal is not included within the scope of computer-readable storage media.

Retention of information such as computer-readable or computer-executable instructions, data structures, program modules, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, and/or computer program products embodying some or all of the various wearable pulse pressure wave sensing implementations described herein, or portions thereof, may be stored, received, transmitted, or read from any desired combination of computer-readable or machine-readable media or storage devices and communication media in the form of computer-executable instructions or other data structures. Additionally, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

The wearable pulse pressure wave sensing implementations described herein may be further described in the general context of computer-executable instructions, such as program modules, being executed by a computing device. Generally, program modules include routines, programs, objects, components, data structures, and the like, that perform particular tasks or implement particular abstract data types. The wearable pulse pressure wave sensing implementations may also be practiced in distributed computing environments where tasks are performed by one or more remote processing devices, or within a cloud of one or more devices, that are linked through one or more communications networks. In a distributed computing environment, program modules may be located in both local and remote computer storage media including media storage devices. Additionally, the aforementioned instructions may be implemented, in part or in whole, as hardware logic circuits, which may or may not include a processor.

Alternatively, or in addition, the functionality described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), and so on.

3.0 Other Implementations

It is noted that any or all of the aforementioned implementations throughout the description may be used in any combination desired to form additional hybrid implementations. In addition, although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What has been described above includes example implementations. It is, of course, not possible to describe every conceivable combination of components or methodologies for purposes of describing the claimed subject matter, but one of ordinary skill in the art may recognize that many further combinations and permutations are possible. Accordingly, the claimed subject matter is intended to embrace all such alterations, modifications, and variations that fall within the spirit and scope of the appended claims.

In regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the foregoing implementations include a system as well as a computer-readable storage media having computer-executable instructions for performing the acts and/or events of the various methods of the claimed subject matter.

There are multiple ways of realizing the foregoing implementations (such as an appropriate application programming interface (API), tool kit, driver code, operating system, control, standalone or downloadable software object, or the like), which enable applications and services to use the implementations described herein. The claimed subject matter contemplates this use from the standpoint of an API (or other software object), as well as from the standpoint of a software or hardware object that operates according to the implementations set forth herein. Thus, various implementations described herein may have aspects that are wholly in hardware, or partly in hardware and partly in software, or wholly in software.

The aforementioned systems have been described with respect to interaction between several components. It will be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (e.g., hierarchical components).

Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

4.0 Claim Support and Further Implementations

The following paragraphs summarize various examples of implementations which may be claimed in the present document. However, it should be understood that the implementations summarized below are not intended to limit the subject matter which may be claimed in view of the foregoing descriptions. Further, any or all of the implementations summarized below may be claimed in any desired combination with some or all of the implementations described throughout the foregoing description and any implementations illustrated in one or more of the figures, and any other implementations described below. In addition, it should be noted that the following implementations are intended to be understood in view of the foregoing description and figures described throughout this document.

In one implementation, a wearable pulse pressure wave sensing device includes a mounting structure which is attachable to a user on an area proximate to an underlying artery; an array of pressure sensors disposed on the mounting structure, each of which is capable of being mechanically coupled to the skin of the user proximate to the underlying artery; and one or more arterial location sensors disposed on the mounting structure which identify a location on the user's skin likely overlying the artery. The pulse pressure wave is measured using the pressure sensor of the array closest to the identified location.

In one implementation, the pressure sensors in the array of pressure sensors are coated with a skin-sensor interface material having a shape which protrudes from the mounting structure so as to contact the skin of the user whenever the wearable pulse pressure wave sensing device is worn by the user. In one version, the pressure sensors of the array of pressure sensors are individually coated with the skin-sensor interface material. In another version, two or more pressure sensors in the array of pressure sensors are collectively coated with the skin-sensor interface material. In one version, one or more of the coated pressure sensors include a single skin interfacing and arterial pressure wave movement transmission layer that is made of a material that is comfortable on the skin of the user and efficiently transmits arterial pressure wave movement. In another version, one or more of the coated pressure sensors include a multi-layer construction including a skin interfacing layer made of a material that is comfortable on the skin of the user, and a layer disposed between the skin interfacing layer and the pressure sensor that is made of a material that efficiently transmits arterial pressure wave movement. As indicated previously, the implementations and versions described in any of the previous paragraphs in this section may also be combined with each other, and with one or more of the implementations and versions described prior to this section. For example, some or all of the preceding implementations and versions may be combined with the foregoing implementation where one or more of the coated pressure sensors include a single skin interfacing and arterial pressure wave movement transmission layer, or where one or more of the coated pressure sensors include a multi-layer construction.

In one implementation, one or more of the pressure sensors include an apparatus that extends and retracts to vary the distance the coated pressure sensor protrudes from the mounting structure. In one version, the apparatus includes at least one of a spring-loaded pogo pin, or an electro-mechanical actuator, or a micro-fluidic pump with a fluid-filled or air-filled bladder. As indicated previously, the implementations and versions described in any of the previous paragraphs in this section may also be combined with each other, and with one or more of the implementations and versions described prior to this section. For example, some or all of the preceding implementations and versions may be combined with the foregoing implementation where one or more of the pressure sensors include an apparatus that extends and retracts to vary the distance the coated pressure sensor protrudes from the mounting structure.

In one implementation, the aforementioned one or more arterial location sensors identify a location on the user's skin in the area proximate to the underlying artery which exhibits the greatest displacement of the user's skin as the location likely overlying the artery. In one version, the arterial location sensors include reflected optical sensors or ultrasonic sensors.

In one implementation, wearable pulse pressure wave sensing device further includes one or more non-arterial motion sensors disposed on the mounting structure which measure the motion of the user's body in the area proximate to the underlying artery that is not caused by motion of the artery. A signal or signals output from the one or more non-arterial motion sensors representing the non-arterial motion of the user's body in the area proximate to the underlying artery are employed to remove a portion of a signal output from the pressure sensor of the array identified as being most closely overlying the likely location of the artery attributable to non-arterial motion. In one version, the one or more non-arterial motion sensors include an accelerometer or gyroscope, or both.

In one implementation, the aforementioned mounting structure includes a band which is either adhered to the area proximate to the underlying artery, or wrapped around and tightened against the area. In one version, the area proximate to the underlying artery is the user's wrist.

In one implementation, a wearable pulse pressure wave sensing device is used in a process for measuring a pulse pressure wave travelling through an artery. The wearable pulse pressure wave sensing device includes an array of pressure sensors which are mechanically coupled to the skin of a user proximate to the artery. The process uses a computing device to perform the following process actions. One or more arterial location sensors of the wearable pulse pressure wave sensing device are employed to identify a location on the user's skin in the area proximate to the artery which exhibits the greatest displacement of the user's skin when a pulse pressure wave passes through the artery in the area. It is then determined which pressure sensor of the array of pressure sensors is closest to the identified location on the user's skin, and the pressure sensor determined to be closest to the identified location is selected. A pulse pressure wave travelling through the artery is then measured using the selected pressure sensor.

In one implementation, the process action of employing one or more arterial location sensors to identify a location on the user's skin in the area proximate to the artery which exhibits the greatest displacement of the user's skin when a pulse pressure wave passes through the artery in the area, includes the actions of employing multiple arterial location sensors to measure the displacement of the user's skin when a pulse pressure wave passes through the underlying artery, each arterial location sensor being associated with and located adjacent to a different pressure sensor of the array of pressure sensors; identifying which of the multiple arterial location sensors measures the greatest displacement of the user's skin when a pulse pressure wave passes through the artery; and designating a location on the user's skin where the identified arterial location sensor measured the greatest displacement of the user's skin as a probable location of the underlying artery. In one version, the process action of determining which pressure sensor of the array of pressure sensors is closest to the identified location on the user's skin, includes the actions of identifying the pressure sensor associated with the arterial location sensor that measured the greatest displacement of the user's skin when a pulse pressure wave passes through the artery; and designating the identified pressure sensor as the closest pressure sensor to the underlying artery.

In one implementation, the process actions of employing one or more arterial location sensors to identify a location on the user's skin in the area proximate to the artery which exhibits the greatest displacement of the user's skin when a pulse pressure wave passes through the artery in the area, and determining which pressure sensor of the array of pressure sensors is closest to the identified location on the user's skin, include the following actions. One or more arterial location sensors are employed to measure the displacement of the user's skin when a pulse pressure wave passes through the underlying artery. Each arterial location sensor includes an image-based arterial location sensor that has been calibrated so that pixels in the images captured by the image-based arterial location sensor are mapped to locations relative to each pressure sensor of the array. Images of the user's skin are captured using the one or more arterial location sensors; the captured images are analyzed to visually identify the location of the greatest displacement of the user's skin when a pulse pressure wave passes through the artery; and it is determined which pressure sensor of the array of pressure sensors is closest to the identified location on the user's skin using the mapped locations of the pressure sensors.

In one implementation, a wearable pulse pressure wave sensing device is part of a system for analyzing a pulse pressure wave travelling through an artery of a user. This system includes a band which is either adhered to an area proximate to an underlying artery of the user's body, or wrapped around and tightened against the area; an array of pressure sensors disposed on the band, each of which is mechanically coupled to the skin of the user proximate to the underlying artery; and one or more arterial location sensors disposed on the band which identify a location on the user's skin likely overlying the artery. In addition the system includes a computing device which executes program modules of a computer program. The computing device is directed by the program modules of the computer program to receive signals output from the one or more arterial location sensors; identify a location on the user's skin in the area proximate to the artery which exhibits the greatest displacement of the user's skin when a pulse pressure wave passes therethrough using the received signals output from the one or more arterial location sensors; determine which pressure sensor of the array of pressure sensors is closest to the identified location on the user's skin; select the pressure sensor determined to be closest to the identified location; receive a signal output from the selected pressure sensor when a pulse pressure wave is travelling through the artery; and analyze the received pressure sensor signal. In one version, the program module for analyzing the received pressure sensor signal, includes sub-modules for determining at least one of a heart rate of the user person wearing the pulse pressure wave sensing device, variations in the user's heart rate over time, the user's augmentation index which is computed using a pulse waveform extracted from the received pressure sensor signal, and a time of arrival of the pulse pressure wave which is used in conjunction with other data to calculate pulse transit time or pulse wave velocity or both.

In various implementations, a pulse wave measuring process is implemented by a step for measuring a pulse pressure wave travelling through an artery using a pressure sensor of an array of pressure sensors which are mechanically coupled to the skin of a user proximate to the artery.

For example, in one implementation, the pulse wave measuring process includes using a computing device to perform the following process actions: a step for employing one or more arterial location sensors to identify a location on the user's skin in the area proximate to the artery which exhibits the greatest displacement of the user's skin when a pulse pressure wave passes through the artery in the area; a step for determining which pressure sensor of the array of pressure sensors is closest to the identified location on the user's skin; a step for selecting the pressure sensor determined to be closest to the identified location; and a step for measuring a pulse pressure wave travelling through the artery using the selected pressure sensor.

In various implementations, a wearable pulse pressure wave sensing device is implemented by means for measuring a pulse pressure wave. For example, in one implementation, a wearable pulse pressure wave sensing device includes a mounting means which is attachable to a user on an area proximate to an underlying artery; a pressure sensor array means disposed on the mounting means, each pressure sensor of which is capable of being mechanically coupled to the skin of the user proximate to the underlying artery; and one or more arterial location sensor means disposed on the mounting structure which identify a location on the user's skin likely overlying the artery. The pulse pressure wave is measured using the pressure sensor of the array closest to the identified location.

Wherefore, what is claimed is:

1. A wearable pulse pressure wave sensing device comprising:
    a mounting structure configured to be attachable to a user's skin;
    an array of pressure sensors disposed on the mounting structure;
    one or more image-based arterial location sensors disposed on the mounting structure;
    one or more processors configured to:
        capture, via the one or more image-based arterial location sensors, one or more images of the user's skin, wherein pixels of the one or more images are mapped to locations relative to each pressure sensor of the array;

analyze the one or more images to visually identify a location of greatest displacement of the user's skin when a pulse pressure wave passes through an underlying artery;

based upon the mapped locations of the pixels relative to each pressure sensor of the array, select a single pressure sensor from the array of pressure sensors that is mapped to the identified location;

measure, via the single selected pressure sensor, the pulse pressure wave; and output a waveform of the pulse pressure wave.

2. The wearable pulse pressure wave sensing device of claim 1, wherein the array of pressure sensors is coated with a skin-sensor interface material having a shape which protrudes from the mounting structure so as to contact the user's skin when the wearable pulse pressure wave sensing device is worn by the user.

3. The wearable pulse pressure wave sensing device of claim 2, wherein the skin interface material is configured to transmit arterial pressure wave movement.

4. The wearable pulse pressure wave sensing device of claim 2, wherein each pressure sensor in the array of pressure sensors comprises a multi-layer construction comprising a skin interfacing layer and an intermediate layer disposed between the skin interfacing layer and the pressure sensor, and wherein the intermediate layer is configured to transmit arterial pressure wave movement.

5. The wearable pulse pressure wave sensing device of claim 2, wherein each pressure sensor in the array of pressure sensors comprises an apparatus that extends and retracts to vary a distance that the pressure sensor protrudes from the mounting structure.

6. The wearable pulse pressure wave sensing device of claim 5, wherein the apparatus that extends and retracts to vary the distance that the pressure sensor protrudes from the mounting structure, comprises at least one of a spring-loaded pogo pin, or an electro-mechanical actuator, or a micro-fluidic pump with a fluid-filled or air-filled bladder.

7. The wearable pulse pressure wave sensing device of claim 1, wherein the one or more image-based arterial location sensors comprise reflected optical sensors or ultrasonic sensors.

8. The wearable pulse pressure wave sensing device of claim 1, further comprising:

one or more non-arterial motion sensors disposed on the mounting structure and configured to measure motion of the user's body and output one or more signals indicting the measured motion of the user's body, and wherein the one or more processors are further configured to filter out a non-arterial motion contribution from the measured pulse pressure wave based on the one or more signals output from the one or more non-arterial motion sensors to generate a filtered pulse pressure wave.

9. The wearable pulse pressure wave sensing device of claim 8, wherein the one or more non-arterial motion sensors comprise one or more of an accelerometer and a gyroscope.

10. The wearable pulse pressure wave sensing device of claim 1, wherein the mounting structure comprises a band configured to affix the wearable pulse pressure wave sensing device to the user's skin, and wherein the array of pressure sensors and the one or more image-based arterial location sensors are disposed on the band.

11. The wearable pulse pressure wave sensing device of claim 1, wherein the one or more processors are further configured to turn off the pressure sensors of the array other than the selected single pressure sensor while the single selected pressure sensor is used to measure the pulse pressure wave.

12. A computer-implemented process for measuring a pulse pressure wave travelling through an artery of a user comprising:

receiving one or more images of the user's skin from one or more image-based arterial location sensors, wherein pixels of the one or more images are mapped to locations relative to each pressure sensor of an array of pressure sensors;

analyzing the one or more images to visually identify a location of greatest displacement of the user's skin when the pulse pressure wave passes through an underlying artery;

based upon the mapped locations of the pixels relative to each pressure sensor of the array, selecting a single pressure sensor from the array of pressure sensors that is mapped to the identified location;

measuring, via the single selected pressure sensor, the pulse pressure wave; and outputting a waveform of the pulse pressure wave.

13. The computer-implemented process of claim 12, further comprising:

turning off the pressure sensors of the array other than the selected single pressure sensor while the single selected pressure sensor is used to measure the pulse pressure wave.

14. A wearable pulse pressure wave sensing device, comprising:

a band configured to be wearable by a user on an area proximate to an underlying artery of the user's body;

an array of pressure sensors disposed on the band;

one or more image-based arterial location sensors disposed on the band; and a computing device disposed on the band and configured to:

capture, via the one or more image-based arterial location sensors, one or more images of the user's skin, wherein pixels of the one or more images are mapped to locations relative to each pressure sensor of the array, analyze the one or more images to visually identify a location of greatest displacement of the user's skin when a pulse pressure wave passes through the underlying artery;

based upon the mapped locations of the pixels relative to each pressure sensor of the array, select a single pressure sensor from the array of pressure sensors that is mapped to the identified location, measure, via the single selected pressure sensor, the pulse pressure wave, and output a waveform of the pulse pressure wave.

15. The wearable pulse pressure wave sensing device of claim 14, wherein the computing device is configured to turn off the pressure sensors of the array other than the selected single pressure sensor while the single selected pressure sensor is used to measure the pulse pressure wave.

* * * * *